US006900236B1

(12) United States Patent
Makriyannis et al.

(10) Patent No.: US 6,900,236 B1
(45) Date of Patent: May 31, 2005

(54) CANNABIMIMETIC INDOLE DERIVATIVES

(75) Inventors: Alexandros Makriyannis, Watertown, MA (US); Hongfeng Deng, Acton, MA (US)

(73) Assignee: University of Connecticut, Farmington, CT (US)

( * ) Notice: Subject to any disclaimer, the term of this patent is extended or adjusted under 35 U.S.C. 154(b) by 61 days.

(21) Appl. No.: 10/111,059

(22) PCT Filed: Oct. 18, 2000

(86) PCT No.: PCT/US00/28832
§ 371 (c)(1),
(2), (4) Date: Oct. 21, 2002

(87) PCT Pub. No.: WO01/28557
PCT Pub. Date: Apr. 26, 2001

Related U.S. Application Data
(60) Provisional application No. 60/159,997, filed on Oct. 18, 1999.

(51) Int. Cl.$^7$ .................... A61K 31/405; C07D 209/12; C07D 209/14; C07D 209/18
(52) U.S. Cl. .................. 514/415; 548/483; 548/484
(58) Field of Search .................. 514/415; 548/483, 548/484

(56) References Cited

U.S. PATENT DOCUMENTS

| | | | |
|---|---|---|---|
| 3,041,343 A | 6/1962 | Jucker et al. | |
| 3,465,024 A | 9/1969 | Brownstein et al. | |
| 3,573,327 A | 3/1971 | Miyano | |
| 3,577,458 A | 5/1971 | Brownstein et al. | |
| 3,656,906 A | 4/1972 | Bullock | |
| 3,886,184 A | 5/1975 | Matsumoto et al. | |
| 3,897,306 A | 7/1975 | Vidic | |
| 3,915,996 A | 10/1975 | Wright | |
| 3,928,598 A | 12/1975 | Archer | |
| 3,944,673 A | 3/1976 | Archer | |

(Continued)

FOREIGN PATENT DOCUMENTS

| | | |
|---|---|---|
| EP | 0276732 | 8/1988 |
| EP | 0737671 | 10/1996 |
| EP | 0 860 168 A2 | 8/1998 |
| FR | 2240003 | 5/1975 |
| FR | 2735774 | 1/2000 |
| GB | 2027021 A | 2/1980 |
| JP | 357098228 | 6/1982 |
| JP | 2304080 | 12/1990 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/29007 | 4/2001 |
| WO | WO 01/32169 | 5/2001 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

C–Attached Aminoalkylindoles; Potent Cannabinoid Mimetics; Thomas E. D'ambra et al; Biorganic & Medicinal Chemistry Letters, vol. 6, No. 1 pp. 17–22, 1996.
Evaluation Of Binding In A Transfected Cell Line Expressing A Peripheral Cannabinoid Receptor (CB2): Indentification Of Cannabinoid Receptor Subtype Selective Ligands; Vincent M. Showalter et al; The Journal of Pharmacology and Experimental Therapeutics, vol. 278, No. 3; pp. 989–999. XP 001097918, (1996).
Pharmacological Characterization Of Three Novel Cannabinoid Receptor Agonists In The Mouse Isolated Vas Deferens; Roger G. Pertwee et al; XP–001041044; European Journal of Pharmacology 284 (1995) pp. 241–247.
Aminoalkylindoles: Structure–Activity Relationships Of Novel Cannabiniod Mimetics; Michael A. Eissenstat et al.; XP 000851090; J. Med. Chem 1995, 38, pp. 3094–3105.
Three–Dimensional Quantitative Structure–Activity Relationship Study Of The Cannabimimetic (Aminoalkylindoles Using Comparative Molecular Field Analysis; XP–002212407; Joong–Youn Shim et al; J. Med. Chem 1998; 41, pp. 4521–4532.
AM630, A Competitive Cannabinoid Receptor Antagonist; XP 000653566; Roger Pertwee et al, Life Sciences, vol. 56, Nos. 23/24, pp. 1949–1955, 1995.
Unified Pharmacophoric Model For Cannabinoids And Aminoalkylindoles Derived From Molecular Superimposition Of CB1 Cannabinoid Receptor Agonists CP55244 and WIN55212–2, Joong–Youn Shim et al; American Chemical Society; pp. 165–184; XP–001095771, (1999).
Structure–Activity Relationships of Indole–And Pyrrole–Derived Cannabinoids; XP 001097982; Jenny L. Wiley et al.; The Journal of Pharmacology and Experimental Therapeutics; pp 995–1004; Vol 285; No. 3, (1998).
International Publication WO 97/00860, CB2 Receptor Agonist Compounds; Murielle Rinaldi et al, Published Jan. 9, 1997.
Pacheco M, et al; "Aminoalkylindoles: Actions On Specific G–Protein–Linked Receptors"; J. Pharmacol. Exp. Ther.; vol. 257, No. 1, pp. 170–183 and 172 Table (1991).
Tetko, I. V. et al; "Volume Learning Algorithm Artificial Neural Networks For 3D QSAR Studies"; J. Med. Chem.; vol. 44, No. 15 (2001) pp. 2411–2420, 2413, 2414 Table 1.

(Continued)

*Primary Examiner*—Taofiq Solola
(74) *Attorney, Agent, or Firm*—Alix, Yale & Ristas, LLP

(57) ABSTRACT

Novel cannabimimetic indole derivatives are presented which have preferential high affinities for one of the cannabinoid CB1 CB2 receptor sites. The improved receptor affinity makes these analogs therapeutically useful as medications in individuals and animals for treatment of pain, glaucoma, epilepsy, nausea associated with chemotherapy.

16 Claims, No Drawings

U.S. PATENT DOCUMENTS

| | | |
|---|---|---|
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan |
| 4,176,233 A | 11/1979 | Archer et al. |
| 4,179,517 A | 12/1979 | Mechoulam et al. |
| 4,188,495 A | 2/1980 | Althuis et al. |
| 4,208,351 A | 6/1980 | Archer et al. |
| 4,278,603 A | 7/1981 | Thakkar |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya et al. |
| 4,876,276 A | 10/1989 | Mechoulam et al. |
| 4,885,295 A | 12/1989 | Bell |
| 5,053,548 A | 10/1991 | Tanaka et al. |
| 5,068,234 A | 11/1991 | D'Ambra et al. |
| 5,147,876 A | 9/1992 | Mizuchi et al. |
| 5,284,867 A | 2/1994 | Kloog et al. |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam et al. |
| 5,532,237 A * | 7/1996 | Gallant et al. |
| 5,538,993 A | 7/1996 | Mechoulam et al. |
| 5,605,906 A | 2/1997 | Lau |
| 5,607,933 A | 3/1997 | D'Ambra et al. |
| 5,618,955 A | 4/1997 | Mechoulam et al. |
| 5,624,941 A | 4/1997 | Barth et al. |
| 5,635,530 A | 6/1997 | Mechoulam et al. |
| 5,688,825 A | 11/1997 | Makriyannis et al. |
| 5,744,459 A | 4/1998 | Makriyannis et al. |
| 5,747,524 A | 5/1998 | Cullinan et al. |
| 5,804,601 A | 9/1998 | Kato et al. |
| 5,817,651 A | 10/1998 | D'Ambra et al. |
| 5,872,148 A | 2/1999 | Makriyannis et al. |
| 5,874,459 A | 2/1999 | Makriyannis et al. |
| 5,925,628 A | 7/1999 | Lee et al. |
| 5,925,768 A | 7/1999 | Barth et al. |
| 5,932,610 A | 8/1999 | Shohami et al. |
| 5,948,777 A | 9/1999 | Bender et al. |
| 6,013,648 A | 1/2000 | Rinaldi et al. |
| 6,028,084 A | 2/2000 | Barth et al. |
| 6,096,740 A | 8/2000 | Mechoulam et al. |
| 6,127,399 A | 10/2000 | Yuan |
| 6,166,066 A | 12/2000 | Makriyannis et al. |
| 6,284,788 B1 * | 9/2001 | Mittendorf et al. |
| 6,391,909 B1 | 5/2002 | Makriyannis et al. |
| 6,579,900 B2 | 6/2003 | Makriyannis et al. |
| 6,610,737 B1 | 8/2003 | Garzon et al. |
| 2002/0119972 A1 * | 8/2002 | Leftheris et al. |
| 2003/0120094 A1 | 6/2003 | Makriyannis et al. |
| 2003/0149082 A1 | 8/2003 | Makriyannis et al. |
| 2004/0077649 A1 | 4/2004 | Makriyannis et al. |
| 2004/0077851 A1 | 4/2004 | Makriyannis et al. |
| 2004/0087590 A1 | 5/2004 | Makriyannis et al. |

OTHER PUBLICATIONS

Abadji V., Lin S., Taha G., Griffin G., Stevenson L.A., Pertwee R.G., Makriyannis A.; "(R)–Methanadamie: a chiral novel anandamide possessing higher potency and metabolic stability"; J. Med. Chem.; 37(12); 1889–1893; 1994; CODEN: JMCMAR; ISSN: 0022–2623; XP002040932.

Alo, B.I.; Kandil, A.; Patil, P. A.; Sharp, M. J.; Siddiqui, M. A.; and Snieckus, V. Sequential Directed Ortho Metalation–Boronic Acid Cross–Coupling Reactions. A general Regiospecific Route to Oxygenated Dibenzo[b,d] pyran–6–ones Related to Ellagic Acid, J. Org. Chem. 1991, 56, 3763–3768.

Arnone M., Maruani J., Chaperon P, et al, Selective Inhibition of sucrose and ethanol intake by SR141716, an antagonist of central cannabinoid (CB1) receptors, Psychopharmacal, (1997) 132, 104–106 (abstract only).

Barnett–Norris et al; "Exploration of biologically relevant conformations of anandamide, . . . "; J. Med. Chem.; vol. 41, 4861–4872; 1998.

Beak, P.; Brown, R. A., The Tertiary Amide as an Effective Director of Ortho Lithiation, J. Org. Chem. 1982, 47, 34–36.

Belgaonkar et al; "synthesius of isocoumarins"; Indian J. Chem.; vol. 13, No. 4, 336–338; 1975 (abstract only).

Beltramo M., Stella N., Calignano A., Lin S. Y., Makriyannis A., Piomelli D; "Functional Role Of High–Affinity Anandamide Transport, as Revealed By Selective Inhibition"; Science; vol. 277; 1094–1097; 1997.

Berdyshev EV, Cannabinoid receptors and the regulation of immune response. Chem Phys. Lipids. Nov. 2000; 108(1–2):169–90.

Berglund et al.; "Structural requirements for arachidonylethanolamide interaction with CB1 and CB2 cannabinoid receptors: . . . "; Porstanglandins, leukotrienes and essential fatty acids; 59(2); 111–118; (1998). (abstract only).

Bodnar, V.N., Lozinskii, M.O., Perl'kis, P.S.; "Synthesis fo 2,5–disubstituted 1,3,4–oxadiazoles and 1,4–dihydro–1,2,4, 5–tetrazines", Ukrainskii Khimicheskii Zhurnal (Russian Edition); 48(12); 1308–1311; 1982 (abstract only).

Bracey, M et al, Structural Adaptations in a Membrane Enzyme That Terminates Endocannabinoid Signaling. Science 2002, 298(5599): 1793–1796.

Brenneisen R, Pgli A, Elsohly MA, Henn V. Spies Y: The effect of orally and rectally administered Δ9–tetrahydrocannabinol on spasticity, a pilot study with 2 patients. Int. J. Pharmacol Ther. (1996) 34:446–452. (abstract only).

Brown et al; "Synthesis and hydroboration of (–)–2–phenylapopinene, Comparison of mono(2–phenylapoisopinocarmpheyl)borane with its 2–methyl and 2–ethyl analogues for the chiral hydrocarboration of representative alkenes", J. Org. Chem.; 55(4); 1217–1223; (1990).

Buckley NE, McCoy KI, Mpzey E et al, "Immunomodulation by cannabinoids is absent in mice deficient for the cannabinoid CB2 receptor"; Eur. J. Pharmacol (2000) 396:141–149.

Burstein et al; "detection of cannabinoid receptors . . . "; Biochem. Biophys. Res. Commun.; vol. 176(1); 492–497; 1991 (abstract only).

Busch–Peterson et al; "Unsaturated side chain beta–11–hydroxyhexahydrocannabinol analogs"; J. Med. Chem.; 39; 3790–3796; (1996).

Calignano A, La Rana G. Diuffrida A, Piomelli D; "Control of pain initiation by endogenous cannabinoids"; Nature (1998) 394:277–291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1–R2.

Calignano A., La Rana G., Makriyannis A., Lin S., Beltramo M., Piomelli D; "Inhibition of Intestinal Motility by Anandamide, an Endogenous Cannanbinoid"; Eur. J. Pharmacol.; 1997; 340 R7–R8.

Campbell FA et al; "Are cannabinoids an effective and safe treatment option in the management of pain? A qualitative systematic review"; BMJ. Jul. 7, 2001;323(7303):13–6.

Charalambous A. et al; "5'-azido $\Delta 8$-THC: A Novel Photoaffinity Label for the Cannabinoid Receptor"; J. Med. Chem., 35, 3076–3079 (1992).

Charalambous A. et al; "Pharmacological evaluation of halogenated . . ."; Pharmacol. Biochem. Behav.; vol. 40; No. 3; 509–512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099–3102, (1973) (abstract only).

Cherest M., Luscindi X.; "The action of acetyl chloride and of acetic anhydride on the lithium nitronate salt of 2–phenylnitroethane . . ."; Tetrahedron; 42(14); 3825–3840; 1986; in French with English abstract.

*1* Cherest M., Lusinchi X.; "A novel electrophilic N–amidation via electron deficient complexes: action of ferric chloride on N–acetyloxyamides"; Tetrahedron Letters; 30(6); 715–718; 1989.

Colombo G, Agabio R, Diaz G. et al; "Appetite suppression and weight loss after the cannabinoid antagonist SR141716"; Life Sci. (1998) 63–PL13–PL117. (abstract only).

Compton et al; "Synthesis and pharmacological evaluation of ether and related analogues of delta8–. delta9– and delta9,11–tetrahydrocannabinol"; J. Med. Chem; vol. 34; No. 11; 3310–3316; 1991.

Consroe P, Musty R, Rein J, Tillery W, Pertwee R; "The perceived effects of smoked cannabis on patents with multiple sclerosis"; Eur. Neurol. (1997) 38–44–48. (abstract only).

Coxon et al; Aust. J. Chem.; 23; 1069–1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967–972; 1993.

*1* Demuynck L. et al; "Rearrangement of Indolo[2,3–a]quinolizidines to derivatives with E–azaaspidospermane skeleton"; Tetrahedron Letters; 30(6) 710–722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375–8380.

Desarnaud F., Cadas H., Piomelli D.; "Anandamide amidohydrolase activity in rat brain microsomes"; J. Biol. Chem.; 270; 6030–6035; (1995).

Deutsch D.G. et al; "Fatty acid sulfonyl fluorides inhibit anandamide metabolism and bind to cannabinoid receptor"; Biochem. Biophys. Res. Commun. 231(1); 217–221; 1997; CODEN: BBRCA9; ISSN:0006–291X; XP002040933.

Deutsch D.G., Chin S.A.; "Enzymatic synthesis and degradation of anandamide, a cannabinoid receptor agonist"; Biochemistry Pharmacology; 46(5); 791–796; 1993.

Devane, W.A. et al; "Determination and Characterization of a Cannabinoid Receptor in a Rat Brain"; Mol. Pharmacol., 34, 605–613 (1988) (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521–528.

Dominiami et al; "Synthesis of 5–(tert–Alkyl)resorcinols"; J. Org. Chem. 42(2); 344–346; (1977).

Drake et al, "classical/nonclassical hybrid cannabinoids"; J. Med. Chem.; vol. 41(19); 3596–3608 (1998).

Edery et al; "Activity of novel aminocannabinoids in baboons"; J. Med. Chem.; 27; 1370–1373 (1984).

Fahrenholtz, K. E., Lurie, M. and Kierstead, AR. W.; "The Total Synthesis of dl–$\Delta 9$–Tetrahydrocannabinol and Four of Its Isomers"; J. Amer. Chem. Soc. 1967, 89(23), 5934–5941.

Fahrenholtz; "the synthesis of 2 metabolites . . . "; J. Org. Chem.; vol. 37(13); 1972; XP002111824.

Fisera, L., Kovac, J., Lesco, J., Smahovsky, V.; "Furan derivatives. Part CLVI. 1,3–dipolar cycloadditions of heterocycles. V. Reaction of C–acetyl–N–phenylnitrilimine with furan derivatives"; Chemicke Zvesti; 35(1); 93–104 1981 (abstract only).

Fride, E. & Mechoulam, R.; "Pharmacological activity of the cannabinoid receptor agonist, anandamide, a brain constituent"; European Journal of Pharmacology, vol. 231; 313–314; 1993.

Galiegue S et al. ; "Expression of central and peripheral cannabinoid receptors in human immune tissues and leukocyte subpopulations"; Eur J Biochem.; Aug. 15, 1995;232(1):54–61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189–194.

Gold et al; "A comparison of the discriminative stimulus properties of delta9–tetrahydrocannabinol and CP 55,940 in rats and rhesus monkeys"; J. Pharmacol. Exp. Ther.; vol. 262(2); 479–486; 1992.

Hampson, A.J., Grimaldi, M. Axpirod J. Wink D; "Cannabidiol and (–) $\Delta 9$ tetrahydrocannabinol are neuroprotective antioxidants"; Proc. Natl Acad Sci. USA (Jul. 1998) 95; 8268–8273.

Hargreaves, K. et al; "A new sensitive method for measuring thermal nociception in cutaneous hyperalgesia"; Plain; 32; 77–88; (1988) (abstract only).

Herzberg U, Eliav E, Bennett GJ, Kopin IJ; "The analgesic effects of R(+) WIN 55,212–2 mesylate, a high affinity cannabinoid agonist in a rat model of neuropathic pain"; Neurosci. Letts. (1997) 221; 157–160.

Hillard C. J., Edgemond, W. S., Jarrahian W., Campbell, W. B; "Accumulation N–Arachidonoylethanolamide (Anandamide) into Cerebellar Granule Cells Occurs via Facilitated Diffusion"; Journal of Neurochemistry; 69; 631–638 (1997).

Horrevoets A.J.G et al; "Inactivation of *Escherichia coli* outer membrane phospholipase A by the affinity label hexadecanesulfonyl fluoride"; Eur. J. Biochem.; 198; 247–253; 1991.

Horrevoets A.J.G et al; "Inactivation of reconstituted *Escherichia coli* outer membrane phospholipase A by membrane–perturbing peptides results in an increased reactivity towards the affinity label hexadecanesulfonyl fluoride"; Eur. J. Biochem.; 198; 255–261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174–2181; XP001097394.

Howlett et al; "Stereochemical effects of 11–OH–delta 8 tetrahydrocannabinol–dimethylheptyl to inhibit adenylate cyclase and bind to the cannabinoid receptor"; Neuropharmacology; vol. 29(2); 161–165; 1990.

Huffman et al; "3-(1',1'-dimethybutyl)—deoxy–delta 8THC and related compounds: synthesis of selective ligands for the CB2 receptor"; Bioorganic and Medicinal Chemistry; vol. 7; 2905–2914; (1999).

Huffman et al; "Stereoselective synthesis of the epimeric delta 7–tetrahydocannabinols"; tetrahedron; vol. 51(4); 1017–1032; (1995).

Huffman et al; "Synthesis of 5',11 dihydroxy delta 8 tetrahydrocannabinol"; Tetrahedron, vol. 53(39), pp. 13295–13306 (1997).

Huffman et al; "Synthesis of a tetracyclic, conformationally constrained analogue of delta8–THC"; Bioorganic & Medicinal Chemistry; vol. 6(12); 2281–2288; 1998; XP002123230.

Huffman et al; "Synthesis of both enantiomers of Nabilone from a common intermediate. Enantiodivergent synthesis of cannabinoids"; J. Org. Chem.; 1991, 56, 2081–2086.

Kaminski NE; "Regulation of the cAMP cascade, gene expression and immune function by cannabinoid receptors"; J Neuroimmunol. Mar. 15, 1998;83(1–2):124–32.

*1* Kawase M. et al; "Electrophilic aromatic substitution with N–methoxy–N–acylnitrenium ions generated from N–chloro–N–methoxyamides: synthesis of nitrogen heterocyclic compounds bearing a N–methoxyamide group"; J. Org. Chem.; 54; 3394–3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515–4519; (1996).

*1* Khanolkar et al; "Molecular probes for the cannabinoid receptors"; Chemistry and Physics of Lipids; 108; 37–52; (2000).

Klein T.W. et al, "The cannabinoid system and cytokine network"; Proc Soc Exp Biol Med. Oct. 2000; 225(1):1–8; (abstract only).

Klein TW et al, "Cannabinoid receptors and immunity"; Immunol Today; Aug. 1998; 19(8):373–81.

Koutek B. et al; "Inhibitors of arachidonyl ethanolamide hydrolysis"; J. Biol. Chem.; 269(37); 22937–40; 1994; CODEN: JBCHA3; ISSN: 0021–9258; XP002040931.

Kumar RN, et al; "Pharmacological actions and therapeutic uses of cannabis and cannabinoids"; Anesthesia, 2001, 56: 1059–1068 (abstract only).

Lan, R et al; "Structure activity relationships of pyrazole derivatives as cannabinoid receptor antagonists"; J. Med. Chem.; vol. 42(4); 769–776; (1999).

Lavalle et al; "Efficient conversion of (1R, 5R)–(+)–alpha–pinene to (1S, 5R)–(–)–nopinene"; J. Org. Chem.; vol. 51(8); 1362–1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure–Activity Studies Related to 1,2–Dimethylheptyl Derivatives"; J. Med. Chem.; vol. 16(11); 1200–1206; 1973.

Lozinsjii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635–2637; 1990 (abstract only).

Ludt, R.E. et al; "A comparison of the synthetic utility of n–butyllithium and lithium dissopropylamide in the metalations of N,N–dialkyltouamides"; J. Org. Chem.; 38(9); 1668–1674 (1973).

Mackie K., Devane W.A., Hille B.; "Anandamide, an endogenous cannabinoid, inhibits calcium currents as a partial agonist in N18 neuroblastoma cells"; Mol. Pharmacol; 44; 498–0503 (1993).

Martin et al; "Behavioral, biochemical, and molecular modeling evaluations of cannabinoid analogs"; Pharmacol. Biochem. Behav.; vol. 40(3); 471–478; 1991.

Martyn CN. Illis LS, Thom J.; "Nabilone in the treatment of multiple sclerosis"; Lancet (1995) vol. 345; p. 579.

Matsumoto et al; "Cannabinoids 1.1–amino–and 1 mercapto–7,8,9,10–tetrahydro–6h–dibenzo[b,d]pyrans"; J. of Med. Chem.; vol. 20(1); 17–24; 1977; XP00211825.

Mechoulam et al; "Stereochemical Requirements for cannabinoid activity"; J. Med. Chem.; 23(10); 1068–1072; (1980).

Mechoulam et al; "Synthesis of the individual, pharmacologically distinct, enantiomers of a tetrahydrocannabinol derivative"; Tetrahedron Asymmetry; 1: 311–314; (1990) (abstract only).

Meltzer et al; "An improved synthesis of cannabinol and cannabiorcol"; Synthesis; 1981:985 (1981).

Melvin et al; "Structure–activity relationships for cannabinoid receptor–binding and analgesic activity: studies of bicyclic cannabinoid analogs"; Mol. Pharmacol.; 44(5); 1008–1015 (1993).

Merck Index; 11th edition; "Tetrahydrocannabinols" compound No. 9142; 1989.

Neunhoeffer O., Gottschlich R.; "Acylating activity of O–acylated hydroxylamine derivatives"; Justus Liebigs Ann. Chem.; 736; 100–109; 1970; in German with English abstract.

Novak, J et al; Cannabis, part 27, synthesis of 8–, 10– and 11–oxygenated cannabinoids; J. Chem. Soc. Perkin Trans.; 2867–2871; (1983) (abstract only).

Nye et al; "High affinity cannabinoid binding sites in brain membranes labelled with [H]–5'–trimethylammonium delta8–tetrahydrocannabinol"; J. Pharmacol. Exp. Ther.; vol. 234(3); 784–791; 1985.

*1* Papahatjis et al; "A new ring–forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8–tetrahydrocannabinols"; J. Med. Chem.; 41(7): 1195–1200; (1998).

*1* Pertwee; Pharmacology of cannabinoid CB1 and CB2 receptors; Pharmacol. Ther., vol. 74(2); pp. 129–180; 1997; XP002226467.

Petrov, M.L., Terent'eva, N.A., Potekhin, K.A., Struchkov, Yu. T.; ".alpha.,.beta.–unsaturated thiolates and their analogs in cycloaddition reactions. XVIII. Reaction of (2–phenylethynyl)tellurolates with C–ethoxycarbonyl–N–Phenylnitrilimine"; Zhurnal Organicheskoi Khimii; 29(7); 1372–1378; (1993) (abstract only).

Piomelli D., Beltramo M., Glasnapp S., Lin S.Y., Goutopoulos A., Xiw X–Q., Makriyannis A.; "Structural determinants for recognition and translocation by the anandamide transporter"; Proc. Natl. Acad. Sci. USA; 96; 5802–5807; (1999).

Pitt et al; "The synthesis of Deuterium, carbon–14 and carrier free tritium labelled cannabinoids"; Journal of Labelled Compounds; vol. 11(4): 551–575; 1975; XP002123229.

Razdan et al; "Drugs delivered from cannabinoids. 6. Synthesis of cyclic analogues of dimethylheptylpyran"; J. Med. Chem.; vol. 19(5); 719–721; 1976 (abstract only).

Reggio et al; "Characterization of a region of steric interference at the cannabinoid receptor using the active analog approach"; J. Med. Chem. United States; vol. 36(12); 1761–1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997 40(20); 3228–3233.

Richardson JD, Aanonsen I, Hargreaves KM; "Antihyperalgesic effects of a spinal cannabinoids"; Eur. J. Pharmacol. (1998) 346:145–153.

Richardso JD, Kilo S. Hargreaves KM; "Cannabinoids reduce dryperalgesia and inflammation via interaction with peripheral CB1 receptors"; Pain (1998) 75:111–119.

Rinaldi–Carmona et al; "Biochemical and pharmacological characterization of SR141716A, the first potent and selective brain cannabinoid receptor antagonist"; Life Sci.; vol. 56(23/24); 1941–1947 (1995).

Rinaldi–Carmona et al; "SR141716A, a potent and selective antagonist of the brain cannabinoid receptor"; FEBS Lett.; 350; 240–244; (1994).

Rompp Chemie Lexikon; Falbe and Regitz; "band 1–A–C1, 8"; Aufl, Thieme Verlag; Stuttgart, S 569–570; 1989.

Santus, Maria; "Studies on thioamides and their derivatives. IX. Synthesis of the derivatives of 1,2,4,5–tetrazine"; Acta Polonae Pharmaceutica; 50(2–3); 183–188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278–87.

Shawali, A.S., Albar, H.A.; "Kinetics and mechanism of dehydrochlorination of N–aryl–C–ethoxycarbonyl formohydrazidoyl chlorides"; Canadian Journal Of Chemistry; 64(5); 871–875; 1986 (abstract only).

Smith P.B. et al; "The pharmacological activity of anandamide, a putative endogenous cannabinoid, in mice"; Journal of Pharmacology and Experimental Therapeutics; vol. 270(1):219–227; 1994.

Tius et al; "Conformationally restricted hybrids of CP–55, 940 and HHC: Steroeselective synthesis and activity"; Tetrahedron; 50 (9); 2671–2680; (1994) (abstract only).

Twitchell, W. et al; "Cannabinoids inhibit N– and P/Q type calcium channels in cultured rat hippocampal neurons"; Journal of Neurophysiology; 78(1); 43–50; 1997 (abstract only).

Watanabe, T.; Miyaura, N.; and Suzuki, A.; "Synthesis of Sterically Hindered Biaryls via the Palladium Catalyzed Cross–Coupling Reaction of Arylboronic Acids or their Esters with Haloarenes"; Synlett 1992, 207–210.

Wilson et al; "9–nor–delta8–tetrahydrocannabinol, a cannabinoid of metabolic intersts"; J. Med. Chem.; 17(4); 475–476; (1974).

Wilson et al; "Analgesic properties of the tetrahydrocannabinols, their metabolites and analogs"; J. Med. Chem.; 18(7); 700–703; (1975).

Wilson et al; "9–nor–9–hydrohexahydrocannabinols. Synthesis, some behavioral and analgesic properties, and comparison with the tetrahydrocannabinols"; J. Med. Chem.; 19(9); 1165–1167; (1976).

Yan, Guo et al; "Synthesis and pharmacological properties of 11–hydroxyl–3–(1'–1'–dimethylheptyl(hexahydrocannabinol: a high affinity cannabinoid agonist"; J. Med. Chem.; vol. 37(16); 2619–2622; (1994).

Yan Guo et al; "(–)–11–hydroxy–7'–isothiocyanato–1'–1'dimethylheptyl–delta8–THC: a novel probe for the cannabinoid receptor in the brain"; J. Med. Chem.; 37(23); 3867–3870; (1994).

* cited by examiner

CANNABIMIMETIC INDOLE DERIVATIVES

This application is the National Stage of International Application No. PCT/US00/28832, filed Oct. 18, 2000, which claims the benefit of U.S. Provisional Application No. 60/159,997, filed Oct. 18, 1999.

FIELD OF THE INVENTION

The present invention relates generally to cannabinoid analogs and is more particularly concerned with new and improved indole cannabinoid analogs exhibiting high binding affinities for cannabinoid receptors, pharmaceutical preparations employing these analogs and methods of administering therapeutically effective amounts of the preparations to provide a physiological effect.

BACKGROUND OF THE INVENTION

Classical cannabinoids such as the marijuana derived cannabinoid $\Delta^9$-tetrahydrocannabinol, ($\Delta^9$-THC) produce their pharmacological effects via interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects. See, for example, Pertwee, R. G., *Pharmacology of cannabinoid CB1 and CB2 receptors*, Pharmacol. Ther., (1997) 74:129–180 and Di Marzo, V., Melck, D., Bisogno, T., DePetrocellis, L., *Endocannabinoids: endogenous cannabinoid receptor ligands with neuromodulatory action*, Trends Neurosci. (1998) 21:521–528.

There is considerable interest in developing cannabinoid analogs possessing high affinity for one of the CB1 or CB2 receptors and/or metabolic stability. Such analogs may offer a rational therapeutic approach to a variety of disease states. One class of cannabimimetic analogs encompasses indole derivatives such as the well known aminoalkylindoles represented by WIN 55212-2 {(R)-(+)-[2,3dihydro-5-methyl-3-[(4-morpholinyl)methyl]-pyrrolo[1,2,3-de]-1,4-benzoxazin-6-yl](1-naptha-lenyl)methanone}. Aminoalkylindoles of this type typically have a carbon linked alkylheterocyclic substituent at the indole-1 position, which is believed to be important for their canabimimetic activities. These known materials are not selective for preferential activation of one of the CB1 or CB2 receptors.

SUMMARY OF THE INVENTION

Aminoalkylindoles have been found to act as agonists for the CB1 and CB2 receptors and occasionally as antagonists for the CB1 and CB2 receptors. The invention includes compounds selective for either the CB1 or CB2 receptors. Further, some of the compounds have agonistic or antagonistic properties.

One aspect of the invention includes several novel aminoalkylindole cannabinoid analogs and physiologically acceptable salts thereof. In one embodiment of the invention, straight carbon chains were introduced to the indole-1 position. Different functional groups were also introduced to the straight carbon chains. This embodiment is shown as A.

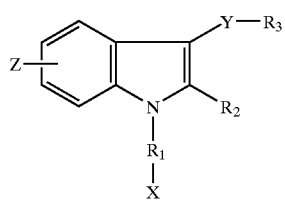

A

Z may be in the 4-, 5-, 6- or 7-position and is selected from nitro; nitroso; amino; alkylamino; dialkylamino; azido ($N_3$); cyano; isothiocyano and phenyl.

X is selected from halogen; hydrogen; hydroxy; lower alkanoate; formyl; amino; cyano; isothiocyano and azido.

$R_1$ is selected from saturated or unsaturated straight carbon chains with a maximum length of seven carbon atoms; saturated or unsaturated branched carbon chains with a maximum length of seven carbon atoms; cyclic aliphatic rings interconnected to the indole-1 position with one or two carbon atoms; bicyclic aliphatic rings interconnected to the indole-1 position with one or two carbon atoms; and heterocyclic rings interconnected to the indole-1 position with one or two carbon atoms.

$R_2$ is selected from H and lower alkyl.

Y is selected from carbonyl and CH=CH (cis or trans).

$R_3$ is selected from phenyl; napthyl; 9-anthracenyl; adamantyl; pyrenyl; phenyl with no more than two substituents selected from halogen, nitro, nitroso, amino, alkylamino, dialkylamino, hydroxy, methoxy, lower alkyl, azido, cyano and isothiocyano; napthyl with no more than two substituents selected from halogen, nitro, nitroso, amino, alkylamino, dialkylamino, hydroxy, methoxy, lower alkyl, azido, cyano and isothiocyano; and 9-anthracenyl with no more than two substituents selected from halogen, nitro, nitroso, amino, alkylamino, dialkylamino, hydroxy, methoxy, lower alkyl, azido, cyano and isothiocyano.

The analogs of this embodiment show high binding affinities for the CB1 and CB2 cannabinoid receptors. More importantly, some of these compounds show not only comparable cannabimimetic activity with the compound WIN 55212-2 but also a surprisingly higher selectivity for one of the CB1 or CB2 receptors. More specifically, the inventive analogs showed similar or higher receptor binding affinity than the well-known indole cannabinoid WIN 55212-2.

Another embodiment of the invention is shown as B. In this embodiment the functionalities of the novel cannabimimetic indole analogs were modified in the indole-3 and/or indole-6 positions.

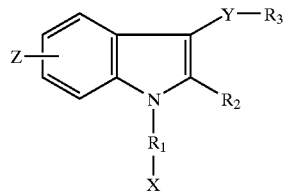

B

Z may be in the 4-, 5-, 6- or 7-position and is selected from halogen; hydroxy; methoxy and lower alkyl.

X is selected from hydrogen; hydroxy; lower alkanoate; formyl; amino; cyano and isothiocyano.

$R_1$ is selected from saturated or unsaturated straight carbon chains with a maximum length of seven carbon atoms; saturated or unsaturated branched carbon chains with a maximum length of seven carbon atoms; cyclic aliphatic rings interconnected to the indole-1 position with one or two carbon atoms; and bicyclic aliphatic rings interconnected to the indole-1 position with one or two carbon atoms.

$R_2$ is selected from H and lower alkyl.

Y is selected from carbonyl and CH=CH (cis or trans).

$R_3$ is selected from phenyl; napthyl; 9-anthracenyl; adamantyl; pyrenyl; phenyl with no more than two substituents selected from halogen, nitro, nitroso, amino, alkylamino, dialkylamino, hydroxy, methoxy, lower alkyl, azido, cyano and isothiocyano; napthyl with no more than two substituents selected from halogen, nitro, nitroso, amino, alkylamino, dialkylamino, hydroxy, methoxy, lower alkyl, azido, cyano and isothiocyano, and 9-anthracenyl with no more than two substituents selected from halogen, nitro, nitroso, amino, alkylamino, dialkylamino, hydroxy, methoxy, lower alkyl, azido, cyano and isothiocyano.

The analogs of this embodiment are surprisingly potent cannabimimetic compounds with high CB1 and/or CB2 selectivity.

Since CB2 selective cannabinoids are able to activate the CB2 receptor and thereby modulate the immune system with little psychoactivity or other CNS effects, these analogs are possible therapeutic agents. Additionally, some of the iodide and fluoride containing analogs are potential radioactive probes for imaging in vivo the distribution of cannabinoid receptors. The azido modified analogs are excellent affinity probes for characterizing binding pockets of cannabinoid receptors.

The analogs disclosed herein are relatively easy to manufacture. Additionally these analogs have better physiochemical properties than naturally occurring cannabinoids. Thus, the novel cannabimimetic indole derivatives described herein, and physiologically acceptable salts thereof, represent potentially useful materials for providing a physiological effect to treat pain, peripheral pain, glaucoma, epilepsy, nausea such as associated with cancer chemotherapy, AIDS Wasting Syndrome, cancer, neurodegenerative diseases including Multiple Sclerosis, Parkinson's Disease, Huntington's Chorea and Alzheimer's Disease, mental disorders such as Schizophrenia and depression; to prevent or reduce endotoxic shock and hypotensive shock; to modulate appetite; to reduce fertility; to prevent or reduce diseases associated with motor function such as Tourette's syndrome; to prevent or reduce inflammation; to provide neuroprotection and to effect memory enhancement.

The novel cannabimimetic indole derivatives described herein also provide useful materials for testing the cannabinoid system. Thus, another aspect of the invention is the administration of a therapeutically effective amount of an inventive compound, or a physiologically acceptable salt thereof, to an individual or animal to provide a physiological effect.

DESCRIPTION OF SOME PREFERRED EMBODIMENTS

As used herein, a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects that result from cannabinoid receptor stimulation include analgesia, decreased nausea resulting from chemotherapy, sedation and increased appetite. Other physiological functions include relieving intraocular pressure in glaucoma patients and suppression of the immune system. Typically, about 10 mg/day to about 1,000 mg/day is a possible "therapeutically effective amount" for the inventive compounds.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

The inventive cannabinoid analogs are generally described by the structural formulas previously disclosed. The following examples are given for purposes of illustration only in order that the present invention may be more fully understood. These examples are not Intended to limit in any way the practice of the invention. The prepared cannabimimetic indole derivatives can generally be described with reference to structural formulas 1 and 2 below and include physiologically acceptable salts thereof.

The inventive cannabimimetic indole derivatives of structural formula 1 include both racemics and two enantiomers.

structural formula 1

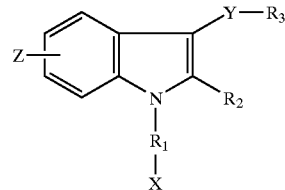

Z is in the indole-6 position and is selected from the group consisting of H; $NO_2$; $NH_2$; $N_3$ and NCS.

$R_1$ is a heterocyclic ring interconnected to the indole-1 position with one carbon atom.

X is hydrogen.

$R_2$ is selected from the group consisting of H and methyl.

Y is carbonyl.

$R_3$ is selected from the group consisting of phenyl; napthyl; adamantanyl; pyrenyl and substituted versions of any of the above.

The inventive materials of structural formula 1 are listed in TABLE 1. It should be noted that $R_1$ for all of the materials of TABLE 1 was 1-(N-Methyl-2-piperidinyl) methyl. All of the materials of TABLE 1 have a chiral center and the binding affinities of the materials of TABLE 1 were obtained by evaluating their racemic samples.

TABLE 1

| | | | | $K_i$ nm | |
|---|---|---|---|---|---|
| analog | Z | $R_2$ | $R_3$ | CB1 | CB2 |
| AM664 | $NO_2$ | $CH_3$ | 2-iodophenyl | 40 | 80.0 |
| AM665 | $NH_2$ | $CH_3$ | 2-iodophenyl | 206 | 20.3 |
| AM671 | $N_3$ | $CH_3$ | Phenyl | 155 | 59.1 |
| AM684 | NCS | $CH_3$ | Phenyl | 181 | 44.8 |
| AM1215 | $N_3$ | $CH_3$ | 2-iodophenyl | 40.7 | 21.9 |
| AM1216 | NCS | $CH_3$ | 2-iodophenyl | 210 | 25.2 |
| AM2209 | $N_3$ | H | 5-azido-2-iodophenyl | 48.8 | 41.8 |
| AM2223 | NCS | H | 5-isothiocyanato-2-iodophenyl | 64.8 | 29.9 |
| AM1221 | $NO_2$ | $CH_3$ | 1-naphthyl | 52.3 | 0.28 |
| AM1225 | $NH_2$ | $CH_3$ | 1-naphthyl | 439.6 | 38.5 |
| AM1231 | $N_3$ | $CH_3$ | 1-naphthyl | 31.2 | 34.2 |
| AM1218 | $NO_2$ | H | 1-naphthyl | 11.2 | 3.98 |
| AM1219 | $NH_2$ | H | 1-naphthyl | 96.6 | 31.3 |
| AM1224 | $N_3$ | H | 1-naphthyl | 20.2 | 0.73 |

TABLE 1-continued

| | | | | $K_i$ nm | |
|---|---|---|---|---|---|
| analog | Z | $R_2$ | $R_3$ | CB1 | CB2 |
| AM1217 | NCS | H | 1-naphthyl | 255 | 81.5 |
| AM1299 | H | H | 4-nitro-1-naphthyl | 12.4 | 13.5 |
| AM1296 | H | H | 1-naphthyl | 7.57 | 3.88 |
| AM1220 | H | H | 1-naphthyl | 3.88 | 73.4 |
| AM2212 | $N_3$ | H | 4-iodo-1-naphthyl | 31.0 | 2.90 |
| AM2215 | NCS | H | 4-isothiocyanato-1-naphthyl | 235 | 99.6 |
| AM1248 | H | H | adamantanyl | 100 | 332 |
| AM1253 | H | H | 2-pyrenyl | 60.3 | 126 |

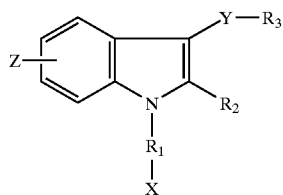

structural formula 2

Z is in the indole-6 position and is selected from the group consisting of hydrogen; $NO_2$; $NH_2$ and halogen.

X is selected from the group consisting of halogen; H; OH; $OCOCH_3$; OTs; NCS; OAc and CN.

$R_1$ is a saturated lower alkane with a maximum length of seven carbon atoms.

$R_2$ is selected from the group consisting of H and methyl.

Y is carbonyl.

$R_3$ is selected from the group consisting of phenyl; napthyl; and substituted versions of any of the above.

The inventive materials of structural formula 1 are listed in TABLE 2. $R_1$ lists the number of carbon atoms in the chain at that position.

TABLE 2

| | | | | | | $K_i$ nM | |
|---|---|---|---|---|---|---|---|
| analog | Z | $R_1$ | X | $R_2$ | $R_3$ | CB1 | CB2 |
| AM623 | H | 4 | H | $CH_3$ | 2-iodophenyl | 272 | 281 |
| AM669 | H | 5 | H | $CH_3$ | 2-iodophenyl | 47.2 | 38.6 |
| AM682 | H | 6 | H | $CH_3$ | 2-iodophenyl | 332 | 693 |
| AM672 | H | 7 | H | $CH_3$ | 2-iodophenyl | 1603 | 1511 |
| AM689 | H | 5 | $OCOCH_3$ | $CH_3$ | 2-iodophenyl | 2279 | 1019 |
| AM690 | H | 5 | OH | $CH_3$ | 2-iodophenyl | 4850 | 1972 |
| AM2227 | H | 5 | OTs | $CH_3$ | 2-iodophenyl | 1024 | 2968 |
| AM2229 | H | 5 | I | $CH_3$ | 2-iodophenyl | 116.5 | 46.2 |
| AM2230 | H | 5 | NCS | $CH_3$ | 2-iodophenyl | 195 | 29.5 |
| AM2225 | H | 5 | F | $CH_3$ | 2-iodophenyl | 5.97 | 3.8 |
| AM679 | H | 5 | H | H | 2-iodophenyl | 13.5 | 49.5 |
| AM692 | H | 5 | $OCOCH_3$ | H | 2-iodophenyl | 2656 | 1519 |
| AM693 | H | 5 | OH | H | 2-iodophenyl | 835 | 526 |
| AM697 | H | 5 | OTs | H | 2-iodophenyl | 1306 | 1116 |
| AM698 | H | 5 | I | H | 2-iodophenyl | 135.8 | 314.7 |
| AM1201 | H | 5 | NCS | H | 2-iodophenyl | 106 | 110 |
| AM694 | H | 5 | F | H | 2-iodophenyl | 0.08 | 1.44 |
| AM1202 | H | 5 | H | H | 2-iodo-5-nitrophenyl | 98.9 | 22.9 |
| AM1203 | H | 5 | H | H | 2-iodo-5-aminophenyl | 63.6 | 88.9 |
| AM1204 | H | 5 | H | H | 2-iodo-5-isothiocyanophenyl | 5659 | 3353 |
| AM1205 | H | 5 | H | H | 2-iodo-5-azidophenyl | 116.9 | 195.7 |
| AM1206 | H | 5 | H | H | 2,5-diiodophenyl | 105.1 | 150.5 |
| AM1284 | H | 3 | $OCOCH_3$ | H | 1-naphthyl | 126.8 | 102.8 |
| AM1289 | H | 3 | OTs | H | 1-naphthyl | 359.6 | 78.64 |
| AM1292 | H | 3 | I | H | 1-naphthyl | 3.1 | 18.1 |
| AM1294 | H | 3 | NCS | H | 1-naphthyl | 283.3 | 237.3 |
| AM1282 | H | 4 | $OCOCH_3$ | H | 1-naphthyl | 133.4 | 100.8 |
| AM1283 | H | 4 | OH | H | 1-naphthyl | 117.2 | 196.5 |
| AM1286 | H | 4 | OTs | H | 1-naphthyl | 1509 | 1289 |
| AM1288 | H | 4 | I | H | 1-naphthyl | 1.3 | 10.5 |
| AM1291 | H | 4 | NCS | H | 1-naphthyl | 2958 | 1804 |
| AM1295 | H | 4 | F | H | 1-naphthyl | 2.5 | 30.7 |
| AM2232 | H | 4 | CN | H | 1-naphthyl | 0.28 | 1.48 |
| AM2231 | $NO_2$ | 4 | CN | H | 1-naphthyl | 4.90 | 23.9 |
| AM2202 | H | 5 | OH | H | 1-naphthyl | 33.1 | 110.6 |

TABLE 2-continued

| analog | Z | $R_1$ | X | $R_2$ | $R_3$ | $K_i$ nM CB1 | $K_i$ nM CB2 |
|---|---|---|---|---|---|---|---|
| AM2203 | H | 5 | I | H | 1-naphthyl | 7.8 | 45.8 |
| AM2204 | H | 5 | NCS | H | 1-naphthyl | 7.5 | 24.4 |
| AM2201 | H | 5 | F | H | 1-naphthyl | 1.0 | 2.6 |
| AM1233 | $NO_2$ | 5 | OAc | H | 1-naphthyl | 141.7 | 153.9 |
| AM1234 | $NO_1$ | 5 | OH | H | 1-naphthyl | 77.6 | 196.8 |
| AM1235 | $NO_2$ | 5 | F | H | 1-naphthyl | 1.5 | 20.4 |
| AM1236 | $NH_2$ | 5 | OAc | H | 1-naphthyl | 1127 | 558.8 |
| AM1237 | $NH_2$ | 5 | OH | H | 1-naphthyl | 836.8 | 244.4 |
| AM1238 | I | 5 | OH | H | 1-naphthyl | 3.1 | 17.3 |
| Am1230 | I | 5 | F | H | 1-naphthyl | 1.1 | 2.4 |
| AM2210 | H | 4 | I | H | 4-nitro-1-naphthyl | 1.8 | 11.3 |
| AM2213 | H | 4 | I | H | 4-azido-1-naphthyl | 3.0 | 30 |
| AM2216 | H | 4 | I | H | 4-isothicocyano-1-napthyl | 42.4 | 213 |
| AM1256 | H | 5 | H | $CH_3$ | 4-dimethylamino-1-napthyl | 4.74 | 18.6 |

The above materials were generally prepared as follows.

A. General Preparation procedures for materials listed in Table 2

The materials listed in Table 2 can be prepared by methods outlined in Scheme 1.

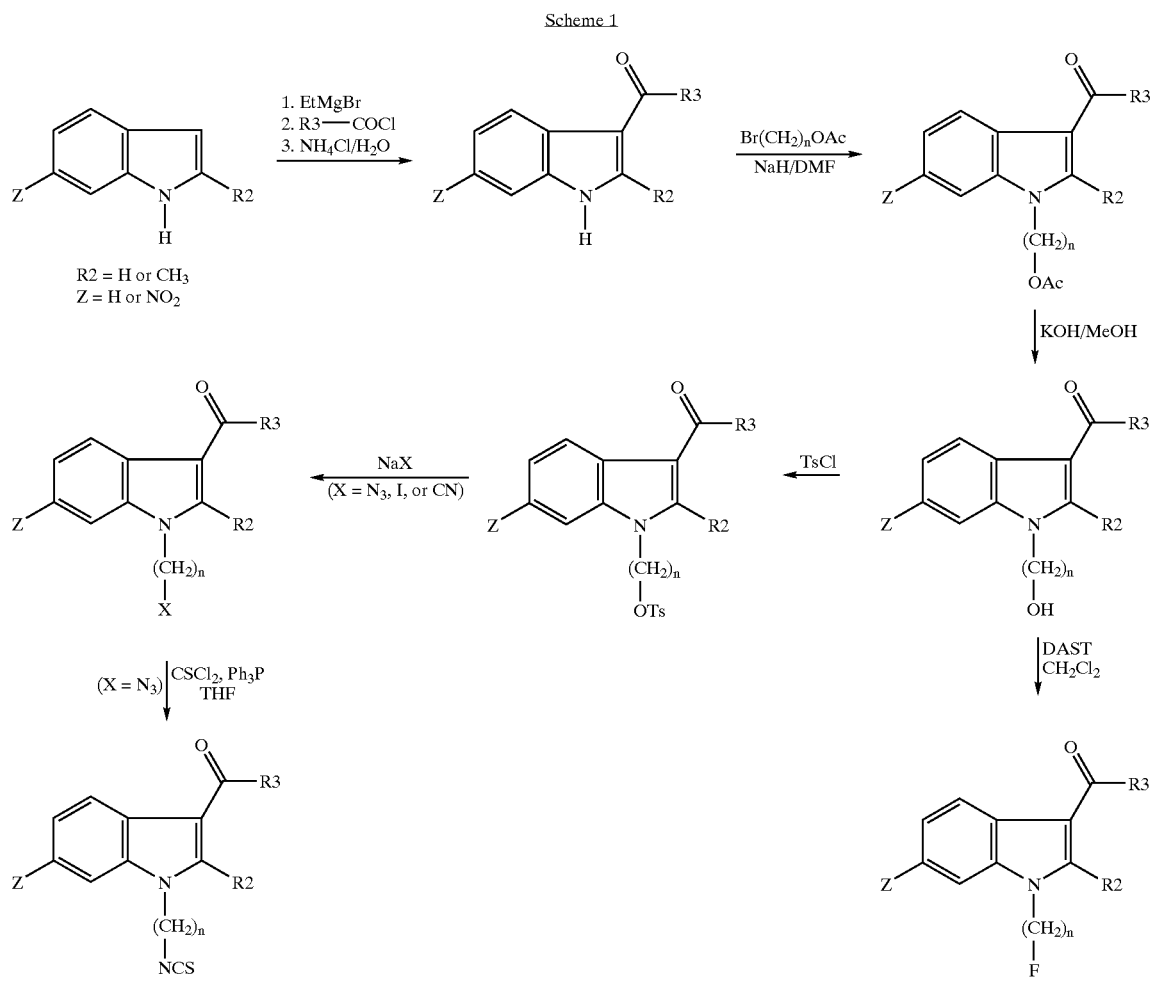

Scheme 1

When Z=NO$_2$, the structures can be transformed to the different substituents as listed in Table 2 using methods outlined in Scheme 2.

Scheme 2

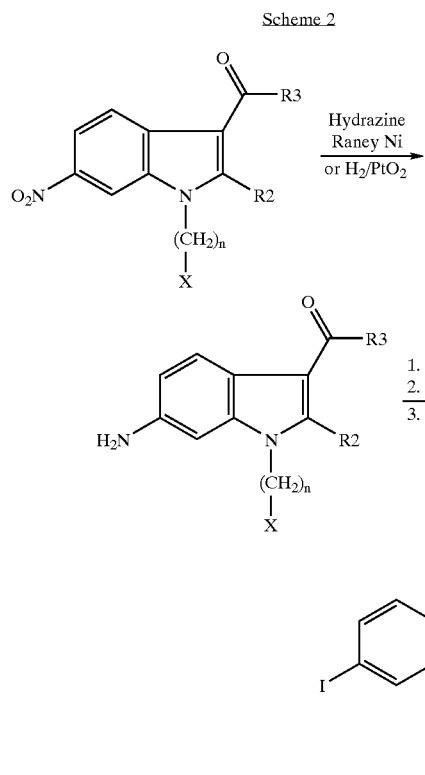

The commercially unavailable R3-COCl used in Scheme 1 can be prepared according to Scheme 3.

Scheme 3

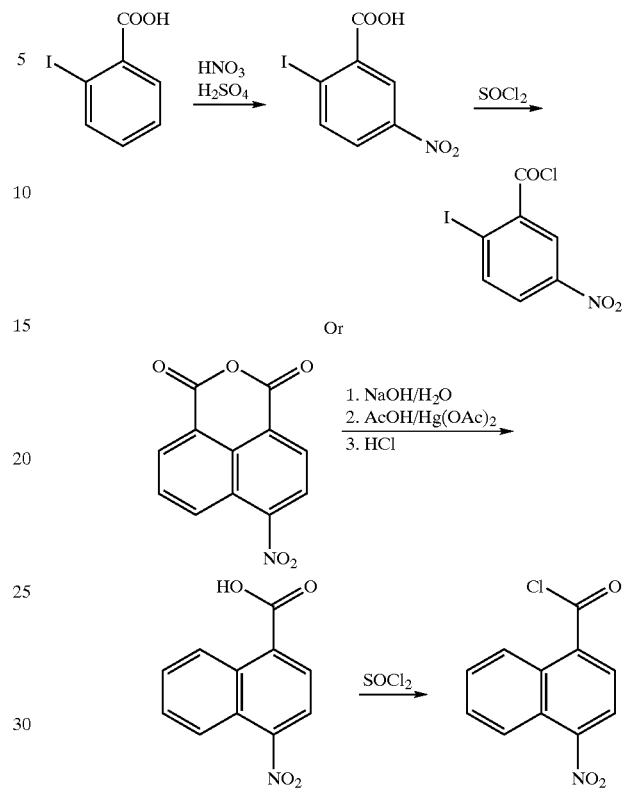

After these acid chlorides were connected to indole 3-position, the nitro group in them can be further transformed into amino, iodo, azido, and isothiocyanate groups according to the methods outlined in Scheme 4.

Scheme 4

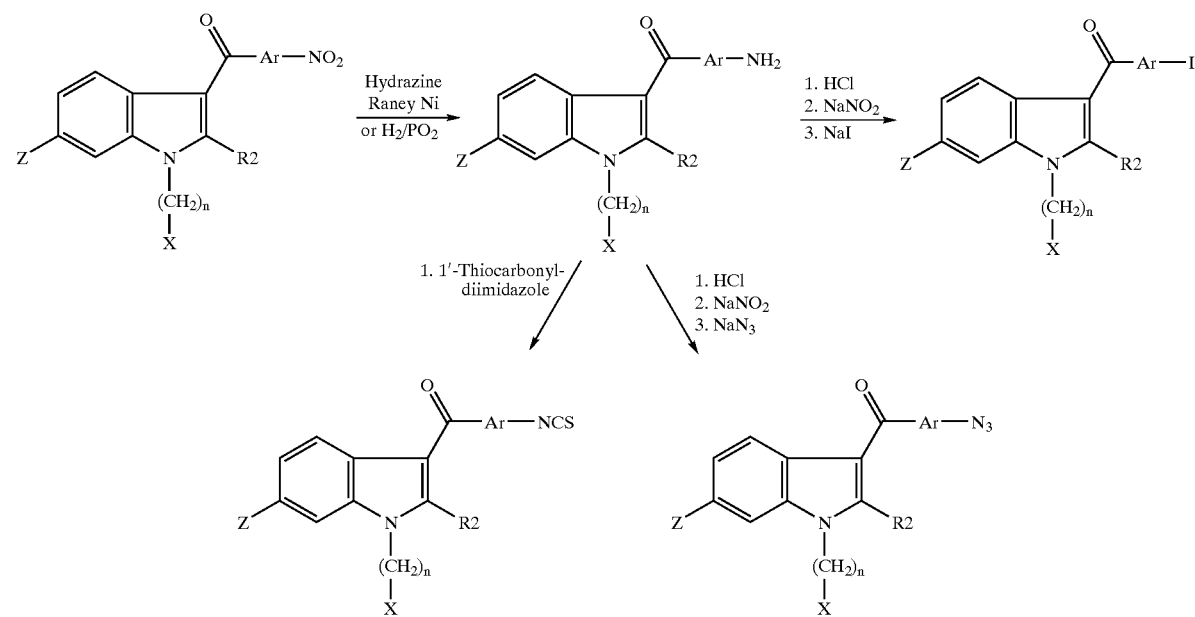

B. General Preparation Procedures for Materials Listed in Table 1

These materials can be prepared in similarly manners as those compounds listed in Table 2 by using N-methyl-2-piperidinemethyl chloride instead of acetoxylalkylhalides for the alkylation of indole 1-position in Scheme 1.

Examples of specific analogs were prepared as follows:

3-Acyl-1H-indole. 17.5 ml of a 3M solution of methyl magnesium bromide in ethyl ether was added dropwise with stirring to a solution of indole (5.85 g, 50 mmol) in 50 mL of ethyl ether at 0° C. After addition, the reaction mixture was warmed up to room temperature and stirred for 2hours (h). Then the reaction mixture was cooled down again to 0° C. and to it was added slowly with violent stirring a solution of acyl chloride (50 mmol) in 50 mL of ethyl ether. The resulting reaction mixture was warmed up to room temperature and stirred for another 1 h followed by the slow addition of 375 ml of ammonium chloride aqueous solution. After violently stirring for 30 min, a white solid was formed and filtrated. The filtrate was washed successively with ethyl ether and recrystallized from ethyl acetate:hexane to afford the product.

2-methyl-3-acyl-1H-indole. The foregoing procedure was repeated using 2-methyl indole in place of indole.

1-Alkyl-2-methyl-3-acyl-1H-indole. To a 1.2 mmol suspension of sodium hydride (48 mg, 60% in mineral oil) in 2 mL of dimethylformamide (DMF) was added 2-methyl-3-acyl-1H-indole (0.4 mmol). After stirring at room temperature for 30 min, alkyl bromide (0.6 mmol) was added dropwise. The resulting mixture was heated to 65° C. and stirred for 3 h followed by removal of solvent under vacuum. The residue was separated by flash column chromatography (silica gel, petroleum ether-ethyl acetate, 5:1, v/v) to afford the product.

A person of ordinary skill in the art, understanding the disclosures for the general preparation and specific preparation examples would know how to modify the disclosed procedures to achieve the above listed analogs.

The materials were tested for CB2 receptor binding affinity and for CB1 receptor affinity (to determine selectivity for the CB2 receptor). As used herein, "binding affinity" is represented by the $IC_{50}$ value which is the concentration of an analog required to occupy the 50% of the total number (Bmax) of the receptors. The lower the $IC_{50}$ value the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. The binding affinities ($K_i$) are expressed in nanomoles (nM) and are listed in TABLE 1 and TABLE 2 above.

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605–813 (1988) and A. Charalambous et al, *5'-azido $\Delta^8$-THC: A Novel Photoaffinity Label for the Cannabinoid Receptor*, J. Med. Chem., 35, 3076–3079 (19921 with the following changes. The above articles are incorporated by reference herein.

Membranes, previously frozen at –80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 µg of membranes were incubated in silanized 96-well microtiter plate with TME containing 0.1% essentially fatty acid-free bovine serum albumin (BSA), 0.8 nM [$^3$H] CP-55,940, and various concentrations of test materials at 200° C. for 1 hour. The samples were filtered using Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099–3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*; Brain Res., 226, 107–118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

The physiological and therapeutic advantages of the inventive materials can be seen with additional reference to the following references, the disclosures of which are hereby incorporated by reference. Arnone M., Maruani J., Chaperon P. et al, *Selective inhibition of sucrose and ethanol intake by SR141716, an antagonist of central cannabinoid (CB1) receptors*, Psychopharmacal, (1997) 132, 104–108. Colombo G. Agabio R, Diaz G. et al: *Appetite suppression and weight loss after the cannabinoid antagonist SR141716*. Life Sci. (1998) 63-PL13-PL117. Simiand J, Keane M, Keane P E, Soubrie P: *SR 141716, A CB1 cannabinoid receptor antagonist, selectively reduces sweet food intake in marmoset*. Behav. Pharmacol (1998) 9:179–181. Brotchie J M: *Adjuncts to dopamine replacement a pragmatic approach to reducing the Problem of dyskinesia in Parkinson's disease*. Mov. Disord. (1998) 13:871–876. Terranova J-P, Storme J-J Lafon N et al: *Improvement of memory in rodents by the selective CB1 cannabinoid receptor antagonist*, SR 141716. Psycho-pharmacol (1996) 126:165–172. Hampson A L Grimaldi M. Axpirod J. Wink D: *Cannabidiol and (–) $\Delta^9$ tetrahydrocannabinol are neuroprotective antoxidants*, Proc. Natl Acad Sci. USA (1998) 9S:8268–8273. Buckley N E, McCoy K I, Mpzey E et al *Immunomodulation by cannabinoids is absent in mice deficient for the cannabinoid $CB_2$ receptor*. Eur. J Pharmacol (2000) 396:141–149. Morgan Dr: *Therapeutic Uses of Cannabis*. Harwood Academic Publishers, Amsterdam. (1997). Joy J E, Wagtson S J, Benson J A: *Marijuana and Medicine Assessing the Science Base*. National Academy Press, Washington, D.C., USA (1999). Shen M. Thayer SA: *Cannabinoid receptor agonists protect cultured rat hippocampal neurons from excitotoxicity*. Mol. Pharmacol (1996) 54:459–462. DePetrocellis L, Melck D, Palmisano A. et al: *The endogenous cannabinoid anandamide inhibits human breaast cancer cell proliferation*, Proc Natl. Acad. Sci USA (1998) 95:8375–8380. Green K. *Marijuana smoking vs. cannabinoids for glaucoma therapy*. Arch. Ophibalmol.

(1998) feb 433–1437. Hemming M, Yellowlees P M, *Effective treatment of Tourette's syndrome with marijuana*. J. Psychopharmacol, (1993) 7:389–391. Muller-Vahl K B, Schneider U, Kolbe H, Emrich, H M. *Treatment of Tourette's syndrome with delta-9-tetrahydrocannabinol*. Am. J. Psychiat. (1999) 156–195. Muller-Vahl K B. Kolbe H, Schneider U, Emrich, H M *Cannabis in movement disorders*. Porsch. Kompicmentarmed (1999) 6 (suppl. 3) 23–27. Consroe P, Musty R, Rein J, Tillery W, Pertwee R. *The perceived effects of smoked cannabis on patents with multiple sclerosis*, Eur. Neurol. (1997) 38–44–48. Pinnegan-Ling D, Musty R. *Marinol and phantom limb pain: a case study*. Proc Inv. Cannabinoid Rea. Sec. (1994):53. Brenneisen R, Pgli A, Elsohly M A, Henn V. Spiess Y: *The effect of orally and rectally administered $\Delta^9$-tetrahydrocannabinol on spasticity, a pilot study with 2 patients*. Int. J. Clin Pharmacol Ther. (1996) 34:446–452. Martyn C N. Iilis L S, Thom J. *Nabilone in the treatment of multiple sclerosis*. Lancet (1995) 345:579. Maurer M, Henn V, Dittrich A, Hofmann A. *Delta-9-tetrahydrocannabinol shows antispastic and analgesic effects in a single case double-blind trial*. Eur. Arch. Psychiat. Clin. Neurosci. (1990), Z40:1–4. Herzberg U, Eliav E, Bennett G J, Kopin I J: *The analgesic effects of R(+) WIN 55.212-2 mesylate, a high affinity cannabinoid agonists in a rare model of neuropathic pain*. Nourosci. Letts. (1997) 221:157–160. Richardson J D, Kilo S. Hargreaves K M, *Cannabinoids reduce dryperalgesia and inflammation via interaction with peripheral CB1 receptors*. Pain (1998) 75:111–119. Richardson J D, Aanonsen I, Hargreaves KM: *Antihyperalgesic effects of a spinal cannabinoids*. Eur. J. Pharmacol. (1998) 346:145–153. Calignano A, La Rana G. Diuffrida A, Piomelli D: *Control of pain initiation by endogenous cannabinoids*. Nature (1998) 394:277–291. Wagner J A, Varga K, Jarai Z, Kunos G: *Mesenteric vasodilation mediated by endothelia anandamide receptors*. Hypertension (1999) 33:429–434. Schuel, H., Burkman, L. J., Picone, R. P., Bo, T., Makriyannis, A., *Cannabinoid receptors in human sperm*. Mol. Biol. Cell., (1997) (8), 325a.

As can be seen from the results in the TABLES, some of the compounds, for example, AM1295, AM1235, AM1288 and AM694, show a high selectivity for the CB1 receptor. Other compounds, for example, AM2230, AM1289, and AM1237, show a high selectivity for the CB2 receptor. The inventive analogs described herein, and physiologically acceptable salts thereof, have high potential when administered in therapeutically effective amounts for providing a physiological effect useful to treat pain, peripheral pain, glaucoma, epilepsy, nausea such as associated with cancer chemotherapy, AIDS Wasting Syndrome, cancer, neurodegenerative diseases including Multiple Sclerosis, Parkinson's Disease, Huntington's Chorea and Alzheimer's Disease, mental disorders such as Schizophrenia and depression; to prevent or reduce endotoxic shock and hypotensive shock; to modulate appetite; to reduce fertility; to prevent or reduce diseases associated with motor function such as Tourette's syndrome; to prevent or reduce inflammation; to provide neuroprotection and to effect memory enhancement. Thus, another aspect of the invention is the administration of a therapeutically effective amount of an inventive compound, or a physiologically acceptable salt thereof, to an individual or animal to provide a physiological effect.

In addition, some of the iodide and fluoride containing compounds, for example, AM694 and AM1230, are potential radioactive probes which would be useful for imaging in vivo the distribution of cannabinoid receptors. Further, azido containing compounds, for example, AM2212, AM2213 and AM1224, would be useful as affinity probes for characterizing binding pockets of cannabinoid receptors.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A compound of the formula:

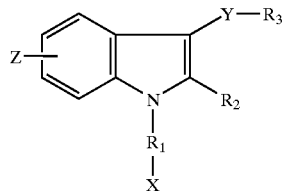

including any optical isomers, and physiologically acceptable salts of the compound or any optical isomer, wherein, Z may be in the 4-, 5-, 6- or 7-position and is selected from nitro, nitroso, amino, alkylamino, dialkylamino, azido, cyano, isothiocyano and phenyl;

X is selected from halogen; hydrogen; hydroxy, lower alkanoate, formyl, amino, cyano, isothiocyano, OTs and azido;

$R_1$ is selected from a saturated or unsaturated C2–C7 straight carbon chain and a saturated or unsaturated C2–C7 branched carbon chain;

$R_2$ is selected from H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

2. The compound of claim 1, wherein Y is C=O.

3. The compound of claim 1, wherein R1 is an alkane with a maximum length of seven carbon atoms.

4. The compound of claim 1, wherein $R_2$ is selected from H and $CH_3$.

5. A method of stimulating a cannabinoid receptor in an individual or animal comprising administering to the individual or animal a therapeutically effective amount of a compound having the formula:

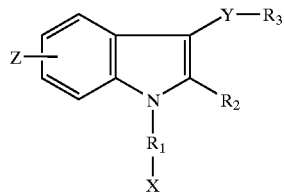

including any optical isomers, and physiologically acceptable salts of the compound or any optical isomer, wherein, Z may be in the 4-, 5-, 6- or 7-position and is selected from nitro, nitroso, amino, alkylamino, dialkylamino, azido, cyano, isothiocyano and phenyl;

X is selected from halogen, hydrogen, hydroxy, lower alkanoate, formyl, amino, cyano, isothiocyano, OTs and azido;

$R_1$ is selected from a saturated or unsaturated C2–C7 straight carbon chain and a saturated or unsaturated C2–$C_7$ branched carbon chain;

$R_2$ is selected from the group consisting of H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano, and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

6. A compound of the formula:

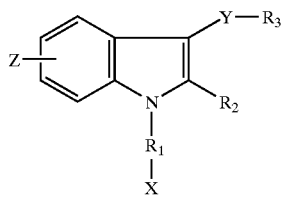

including any optical isomers, and physiologically acceptable salts of the compound or any optical isomer, wherein, Z is selected from hydrogen in the 6-position or halogen in the 4-, 5-, 6- or 7-position;

X is selected from halogen, hydroxy, lower alkanoate, formyl, cyano, and isothiocyano;

$R_1$ is selected from a saturated or unsaturated C2–C7 straight carbon chain and a saturated or unsaturated C2–C7 branched carbon chain;

$R_2$ is selected from H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano, and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

7. The compound of claim 6, wherein $R_1$ is $CH_2$.

8. The compound of claim 6, wherein Y is C=O.

9. The compound of claim 6, wherein $R_2$ is selected from H and $CH_3$.

10. A method of stimulating a cannabinoid receptor in an individual or animal comprising administering to the individual or animal a therapeutically effective amount of a compound having the formula:

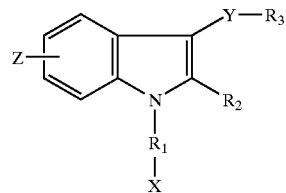

including any optical isomers, and physiologically acceptable salts of the compound or any optical isomer, wherein, Z is selected from hydrogen in the 6-position or halogen in the 4-, 5-, 6- or 7-position;

X is selected from halogen, hydroxy, lower alkanoate, formyl, cyano, and isothiocyano;

$R_1$ is selected from a saturated or unsaturated C2–C7 straight carbon chain and a saturated or unsaturated C2–C7 branched carbon chain;

$R_2$ is selected from H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano, and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

11. A pharmaceutical preparation containing a therapeutically effective amount of a compound having the formula:

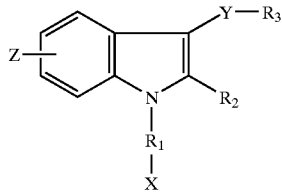

including any optical isomers, and physiologically acceptable salts of the compound or any optical isomer, wherein, Z may be in the 4-, 5-, 6- or 7-position and is selected from nitro, nitroso, amino, alkylamino, dialkylamino, azido, cyano, isothiocyano, and phenyl;

X is selected from halogen; hydrogen; hydroxy, lower alkanoate, formyl, amino, cyano, isothiocyano, OTs and azido;

$R_1$ is selected from a saturated or unsaturated C2–C7 straight carbon chain and a saturated or unsaturated C2–C7 branched carbon chain;

$R_2$ is selected from H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

12. The compound of claim 1, wherein:

Z may be in the 4-, 5- or 7-position and is selected from nitro, nitroso, amino, alkylamino, dialkylamino, azido, cyano, isothiocyano, and phenyl;

X is selected from halogen; hydrogen; hydroxy, lower alkanoate, formyl, amino, cyano, isothiocyano and azido;

$R_1$ is selected from a saturated or unsaturated straight C2–C7 carbon chain and a saturated or unsaturated C2–C7 branched carbon chain;

$R_2$ is selected from H and lower alkyl;

Y is selected from carbonyl and CH=CH (cis or trans); and when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano, or when X is halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

13. A test method, comprising:

providing a cannabinoid compound having the following formula

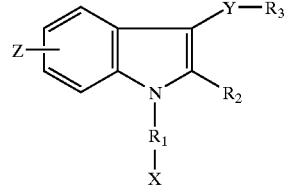

including any optical isomers, and physiologically acceptable salts of the compound or any optical isomer, wherein the cannabinoid compound includes a radioactive moiety and, Z may be in the 4-, 5-, 6- or 7-position and is selected from halogen, hydroxy, methoxy, lower alkyl, nitro, nitroso, amino, alkylamino, dialkylamino, azido, cyano, isothiocyano and phenyl;

X is selected from halogen; hydrogen; hydroxy, lower alkanoate, formyl, amino, cyano, isothiocyano and azido;

$R_1$ is selected from a saturated or unsaturated straight carbon chain with a maximum length of seven carbon atoms, a saturated or unsaturated branched carbon chain with a maximum length of seven carbon atoms, a cyclic aliphatic ring interconnected to the indole-1 position with one or two carbon atoms, a bicyclic aliphatic ring interconnected to the indole-1 position with one or two carbon atoms, and a heterocyclic ring interconnected to the indole-1 position with one or two carbon atoms;

$R_2$ is selected from H and lower alkyl;

Y is selected from carbonyl and CH=CH (cis or trans); and $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano;

binding the cannabinoid compound to a receptor, wherein the radioactive emission provides an indication of the presence of the receptor.

14. The test method of claim 13 wherein the radioactive emission additionally provides an indication of an amount of the receptor.

15. A pharmaceutical preparation containing a therapeutically effective amount of a compound having the formula:

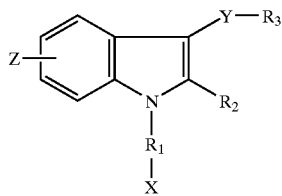

including any optical isomers, and physiologically acceptable salts of the compound or any optical isomer, wherein, Z is selected from hydrogen in the 6-position or halogen in the 4-, 5-, 6- or 7-position;

X is selected from halogen, hydroxy, lower alkanoate, formyl, cyano, and isothiocyano;

$R_1$ is selected from a saturated or unsaturated C2–C7 straight carbon chain and a saturated or unsaturated C2–C7 branched carbon chain;

$R_2$ is selected from H and lower alkyl;

Y is selected from carbonyl and CH=CH (cis or trans); and when X is halogen $R_3$ is selected from phenyl, napthyl, 9-anthracenyl, adamantyl, pyrenyl, phenyl with no more than two substituents selected from nitro, nitroso, amino, alkylamino, dialkylamino, hydroxy, methoxy, lower alkyl, azido, cyano and isothiocyano, napthyl with no more than two substituents selected from nitro, nitroso, amino, alkylamino, dialkylamino, hydroxy, methoxy, lower alkyl, azido, cyano and isothiocyano, and 9-anthracenyl with no more than two substituents selected from nitro, nitroso, amino, alkylamino, dialkylamino, hydroxy, methoxy, lower alkyl, azido, cyano and isothiocyano, or when X is not halogen $R_3$ is selected from phenyl, napthyl, 9-anthracenyl, adamantyl, pyrenyl, phenyl with no more than two substituents selected from halogen, nitro, nitroso, amino, alkylamino, dialkylamino, hydroxy, methoxy, lower alkyl, azido, cyano and isothiocyano, napthyl with no more than two substituents selected from halogen, nitro, nitroso, amino, alkylamino, dialkylamino, hydroxy, methoxy, lower alkyl, azido, cyano and isothiocyano and 9-anthracenyl with no more than two substituents selected from halogen, nitro, nitroso, amino, alkylamino, dialkylamino, hydroxy, methoxy, lower alkyl, azido, cyano and isothiocyano.

16. A compound of the formula:

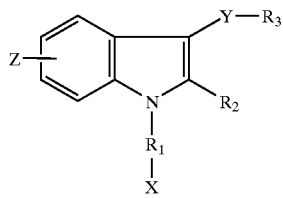

including any optical isomers, and physiologically acceptable salts of the compound or any optical isomer, wherein, Z is selected from nitro, nitroso, amino, alkylamino, dialkylamino, azido, cyano, isothiocyano, phenyl, halogen, OH, methoxy or lower alkyl in the 4-, 5-, 6- or 7-position or hydrogen in the 6-position;

$R_1$ is selected from a saturated or unsaturated straight carbon chain with a maximum length of seven carbon atoms and a saturated or unsaturated branched carbon chain with a maximum length of seven carbon atoms and X is selected from hydroxy, lower alkanoate, formyl, cyano, isothiocyano and azido, or $R_1$ is a saturated or unsaturated straight carbon chain having seven carbon atoms or a saturated or unsaturated branched carbon chain with a maximum length of seven carbon atoms and X is halogen, or $R_1$ is a saturated or unsaturated straight carbon chain having seven carbon atoms or an unsaturated branched carbon chain with a maximum length of seven carbon atoms and X is amino;

$R_2$ is selected from H and lower alkyl;

Y is selected from carbonyl and CH=CH (cis or trans); and $R_3$ is selected from adamantyl, or $R_3$ is selected from phenyl with no more than two substituents selected from nitro, nitroso, amino, alkylamino, dialkylamino, azido and isothiocyano; napthyl with no more than two substituents selected from nitro, nitroso, amino, alkylamino, dialkylamino, azido, and isothiocyano; and 9-anthracenyl with no more than two substituents selected from nitro, nitroso, amino, alkylamino, dialkylamino, azido and isothiocyano, or $R_3$ is selected from disubstituted phenyl with a first substituent selected from halogen, alkylamino, dialkylamino, hydroxy, methoxy, lower alkyl, azido, cyano and isothiocyano and a second substituent independently selected from nitro, nitroso, amino, alkylamino, dialkylamino, azido and isothiocyano; disubstituted napthyl with a first substituent selected from halogen, alkylamino, dialkylamino, hydroxy, methoxy, lower alkyl, azido, cyano and isothiocyano and a second substituent independently selected from nitro, nitroso, amino, alkylamino, dialkylamino, azido and isolthiocyano; or disubstituted 9-anthracenyl with a first substituent selected from halogen, alkylamino, dialkylamino, hydroxy, methoxy, lower alkyl, azido, cyano and isothiocyano and a second substituent independently selected from nitro, nitroso, amino, alkylamino, dialkylamino, azido and isothiocyano.

* * * * *

UNITED STATES PATENT AND TRADEMARK OFFICE
CERTIFICATE OF CORRECTION

PATENT NO. : 6,900,236 B1
DATED : May 31, 2005
INVENTOR(S) : Makriyannis et al.

It is certified that error appears in the above-identified patent and that said Letters Patent is hereby corrected as shown below:

<u>Column 18,</u>
Lines 18 and 22, after "from" delete "halogen".
Line 26, before "nitro" delete "halogen".

<u>Column 19,</u>
Line 59, after "isothiocyano" insert -- , --.

<u>Column 20,</u>
Line 56, delete "isolthiocyano" and insert -- isothiocyano --.

Signed and Sealed this

Eleventh Day of April, 2006

JON W. DUDAS
*Director of the United States Patent and Trademark Office*